Feb. 16, 1960 E. S. BOERNER Plant Pat. 1,909
ROSE PLANT
Filed June 8, 1959
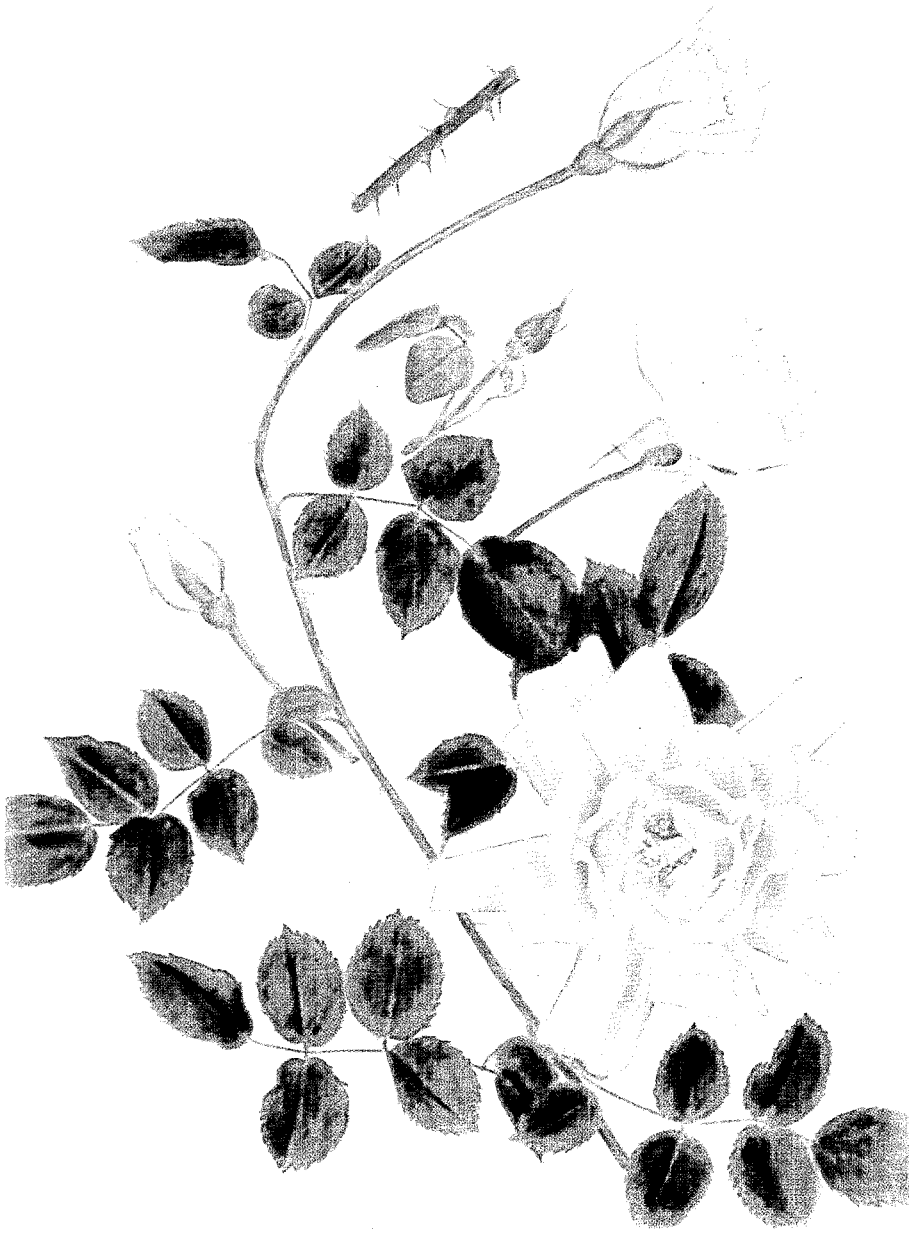
Inventor.
E. S. Boerner
By: Robb & Robb
Attorneys.

United States Patent Office

Plant Pat. 1,909
Patented Feb. 16, 1960

1,909

ROSE PLANT

Eugene S. Boerner, Newark, N.Y., assignor to Jackson & Perkins Company, Newark, N.Y., a corporation of New York Application June 8, 1959, Serial No. 818,988

1 Claim. (Cl. 47—61)

The present invention relates to a new and distinct variety of rose plant of the hybrid tea class, which was originated by me by crossing an unnamed and unpatented seedling of "Lilette Mallerin" (unpatented) × "Brazier" (unpatented) with the variety "Pageant" (Plant Patent No. 1,252).

The primary objective of this breeding was to produce a new rose variety which emphasizes the bicolor "Golden-Red." This objective was approached by crossing the variety "Pageant" and a seedling which originated as the result of the cross of two bicolored varieties, "Lilette Mallerin" × "Brazier," and the objective was fully achieved, along with other desirable characteristics, as evidenced by the following unique combination of features which are outstanding in the new variety and distinguish it from its parents, as well as from all other varieties of which I am aware:

(1) A partial quilling of the outer flower petals while the inner petals remain full;

(2) A good tea fragrance, which is quite unusual in a bicolor rose; and (3) A distinctive and very sharp bicolor general color tonality of the flowers corresponding to golden yellow (Mikado Orange) on the reverse of the petals, and bright red suffused with gold (Scarlet Red, with the lower half of the petal lightly overcast with Cadmium Orange) on the inside of the petals.

Assexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed seedling of "Lilette Mallerin" × "Brazier."

*Pollen parent.*—"Pageant."

Classification:

*Botanic.*—Hybrid tea.

*Commercial.*—Hybrid tea.

*Flower*

(Observations made from specimens grown in a greenhouse at Newark, New York near mid-morning during the middle of June.)

Blooming habit: Recurrent—continuous.

Bud:

*Size.*—Large.

*Form.*—pointed; is not affected by wet or hot weather.

*Color.*—When sepals first divide—Light Cadmium, Plate 4. When petals begin to unfurl—Buff-Yellow, Plate 4. When half-blown: inside of petals—Rose Doree, Plate 1; reverse of petals—Buff-Yellow, Plate 4, lightly overcast with Pinard Yellow, Plate 4.

*Sepals.*—Smooth edge; Curl back when petals begin to unfurl. Color: inside—Light Fluorite Green, Plate 32; outside—Chromium Green, Plate 32.

*Calyx.* — Color — Chromium Green, Plate 32. Shape—funnel. Size—broad. Aspect—smooth. Odor when rubbed—none.

*Peduncle.*—Length—very long. Aspect—smooth. Strength — stiff; slender. Color — Chromium Green, Plate 32.

*Opening.*—Opens up well; is not affected by adverse weather conditions.

Bloom:

*Size.*—Medium. Average size when fully expanded—2½ inches.

*Borne.*—Both singly and several together.

*Stems.*—Medium length; normal strength.

*Form (when first open).*—High center. Permanence—retains its form to the end, but outer petals quill.

*Petalage.*—Double (full but open center). Number of petals under normal conditions—From 25 to 30.

*Color.*—Center of flower—Spectrum Red, Plate 1, lightly overcast with Scarlet, Plate 1. Outer petals—Scarlet Red, Plate 1, lightly overcast with Rose Doree, Plate 1. Base of petals (Aiglet)—Empire Yellow, Plate 4. Inside of petals—Scarlet Red, Plate 1, with lower half of petals lightly overcast with Cadmium Orange, Plate 3. Reverse of petals—Mikado Orange, Plate 3. General tonality from a distance—Scarlet Red, Plate 1.

*Discoloration.*—General tonality at end of first day—Spectrum Red, Plate 1. Second day—Scarlet Red, Plate 1. Third day—Scarlet Red, Plate 1, lightly overcast with Rose Doree, Plate 1.

Petals:

*Texture.*—Thick; is not affected by wet or hot weather.

*Appearance.*—Inside—satiny. Outside—shiny.

*Form.*—Oval: slightly notched.

*Arrangement.* — Imbricated (regularly arranged shingle-like).

*Petaloids in center.*—Few; large.

*Persistence.*—Drop off cleanly.

*Fragrnace.*—Moderate. Nature—tea (average hybrid tea scent).

*Lasting quality.*—On the plant—long. As cut flower—long.

*Genital organs*

Stamens, anthers: Large, many; regularly arranged around styles. Color—Grenadine Red, Plate 2.

Stamens, filaments (threads): Long. Color—Scarlet Red, Plate 1.

Pollen: Color—Capucine Buff, Plate 3.

Styles: Loosely separated; uneven length; short; thin.

Stigmas: Color—Orange-Buff, Plate 3.

Ovaries: All enclosed in calyx.

Hips: None.

Seeds: None.

*Plant*

Form: Bush.

Growth: Vigorous; upright.

Foliage: Compound of 5 to 7 leaflets.

*Size.*—Medium.

*Quantity.*—Normal.

*Color.*—New foliage: upper side—Chromium Green,

Plate 32; under side—Turtle Green, Plate 32. Old foliage: upper side—Bice Green, Plate 17; under side—Light Bice Green, Plate 17.

*Shape.*—Oval pointed.

*Texture.* — Upper side — smooth. Under side — smooth.

*Ribs and veins.*—Ordinary.

*Edge.*—Serrated (saw-toothed).

*Serration.*—Single; small.

*Leaf stem.*—Color—Biscay Green, Plate 17. Under side—prickly.

*Stipules.*—Medium length; smooth.

Wood:

*New wood.*—Color—Oil Green, Plate 5. Bark—smooth.

*Old wood.*—Color—Bice Green, Plate 17. Bark—smooth.

Thorns:

*Thorns.*—Quantity: on main stalks from base—ordinary; on laterals from stalk—ordinary. Form—narrow base; medium length; hooked downward. Color (when young)—Begonia Rose, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a partially quilling habit of the outer flower petals while the inner petals remain full, a good tea fragrance of the flowers, and a distinctive and very sharp bicolor general color tonality of the flowers corresponding to Mikado Orange on the reverse of the petals, and Scarlet Red on the inside of the petals, with Cadmium Orange lightly overcasting the lower half of the petals on the inside.

No references cited.